United States Patent [19]
Thompson et al.

[11] Patent Number: 5,355,211
[45] Date of Patent: Oct. 11, 1994

[54] REFRACTOMETER SUBASSEMBLY METHOD AND APPARATUS

[75] Inventors: Shawn E. Thompson, Grand Island; Lawrence R. Pastwik, Lancaster, both of N.Y.

[73] Assignee: Leica Inc., Buffalo, N.Y.

[21] Appl. No.: 41,869

[22] Filed: Apr. 2, 1993

[51] Int. Cl.[5] .................................. G01N 21/41
[52] U.S. Cl. ................................................ 356/135
[58] Field of Search ................ 356/135, 136, 137; 359/819, 820

[56] References Cited

U.S. PATENT DOCUMENTS

| | | | |
|---|---|---|---|
| 8,509 | 11/1851 | Clarke | 359/819 |
| 2,619,003 | 11/1952 | Polanyi | 356/135 |
| 3,279,309 | 10/1966 | Goldberg | 356/135 |
| 3,329,060 | 7/1967 | Holleran | 356/135 |
| 3,447,875 | 6/1969 | Goldberg | 356/135 |
| 3,625,620 | 12/1971 | Goldberg | 356/135 |
| 3,749,479 | 7/1973 | Kempf | 359/819 |

FOREIGN PATENT DOCUMENTS 2255221  5/1973  Fed. Rep. of Germany ...... 356/135

*Primary Examiner*—Richard A. Rosenberger
*Attorney, Agent, or Firm*—Bean, Kauffman & Spencer

[57] ABSTRACT

An apparatus and method for creating an aligned subassembly of optically critical components of a temperature compensated, hand-held refractometer prior to installing the subassembly in a refractometer housing is disclosed. The preferred embodiment is a plastic subassembly frame with a critical angle prism reference surface, a temperature responsive member fulcrum, a compensating prism mount, an objective lens mount, and a reticle mount.

11 Claims, 2 Drawing Sheets

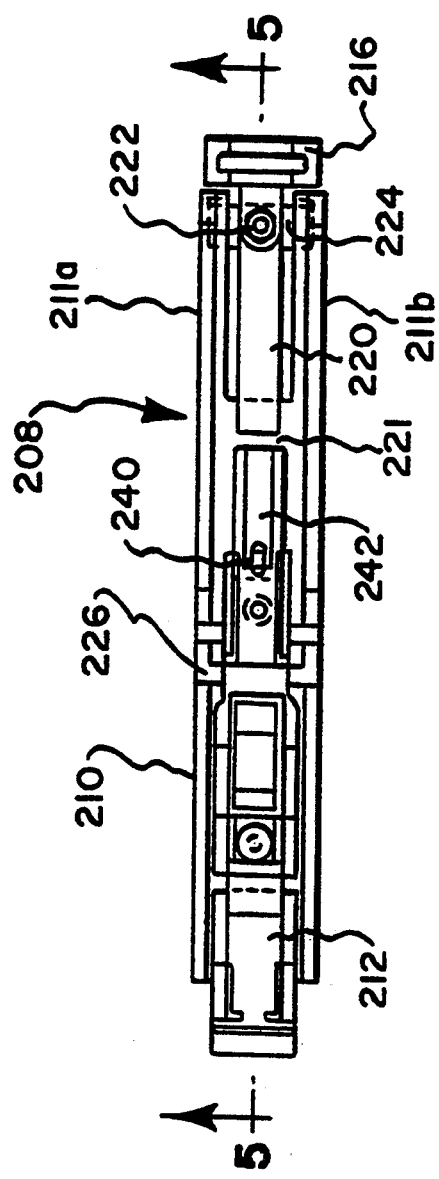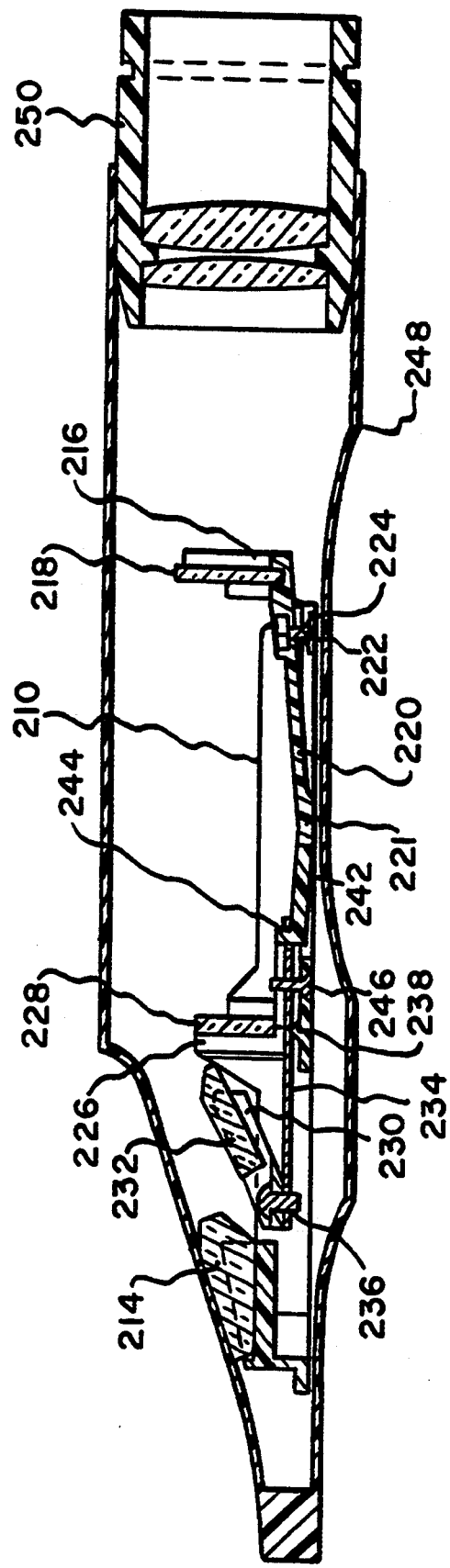

REFRACTOMETER SUBASSEMBLY METHOD AND APPARATUS

BACKGROUND OF THE INVENTION

The present invention relates to refractometers, more particularly temperature compensated, hand-held refractometers, and to methods of aligning optically critical components thereof.

Temperature compensated, hand-held refractometers are well known in industry for measuring the refractive index of a test substance. Since the refractive index of a liquid substance is related to the concentration of elements within the substance, the units of a refractometer scale may be calibrated to indicate quantities which are of practical importance. For example, the sugar concentration in a soft drink or the lubricant concentration in machine tool cutting fluid may be readily measured using a suitably calibrated refractometer.

A common arrangement of optical elements in a temperature compensated hand-held refractometer is described in U.S. Pat. No. 3,329,060. The optical elements include a critical angle prism, a compensating prism or wedge, an objective lens, a reticle, and an eyepiece; a temperature responsive bimetallic member moves the compensating wedge to adjust for ambient temperature variations. It is known that temperature compensation may also be achieved by using a temperature responsive member to move the objective lens, as taught in U.S. Pat. Nos. 3,279,309 and 3,625,620, or the reticle, as taught in U.S. Pat. Nos. 2,619,003 and 3,447,875. Alternatives which do not rely upon mechanically moving parts to effect temperature compensation include refractometers having a liquid filled compensating prism, as disclosed in U.S. Pat. No. 3,267,795. Regardless of the method of temperature compensation, alignment of the optical elements, excluding the eyepiece, is necessary for accurately reporting refractive values.

Prior art refractometers require that alignment be carried out after the optical elements have been placed inside the refractometer housing. In commercial models sold for over twenty years, as well as in currently available models known to applicant, the critical angle prism is affixed in the housing and the other elements are placed in the housing as an unaligned subassembly; alignment is subsequently effected using externally accessible adjustment screws. FIG. 1 shows a prior art refractometer subassembly with a metal strip 10, reticle mount 16 for holding a reticle 18, lens mount 26 for holding an objective lens 28, and compensating wedge mount 30 for holding a compensating wedge 32. Compensating wedge mount 30 is fastened to one end of a temperature responsive member 34, while the other end of member 34 is fastened to strip 10.

Various advantages of the present invention distinguish it from the prior art. Because the subassembly frame is a one piece unit, it may be formed from plastic in a single molding operation. By providing a reference surface on the frame for locating and supporting a critical angle prism, complete and even permanent alignment of the optically critical elements can be achieved before they are installed within the refractometer housing. Thus, if the housing is hermetically sealed to protect the instrument from possible immersion in a test fluid, the invention eliminates the need to access external adjustment screws which may only be reached by breaking the seal.

Accordingly, it is an object of the present invention to allow for complete and durable pre-alignment of the optical elements of a temperature compensated hand-held refractometer prior to installing them as a subassembly inside the refractometer housing.

This and other objects of the invention will be apparent to those skilled in this art from the following detailed description of the invention and the accompanying figures.

SUMMARY OF THE INVENTION AND DRAWINGS

The present invention comprises a temperature compensated, hand-held refractometer with a subassembly frame for supporting a critical angle prism, compensating wedge, objective lens, and reticle such that the wedge, lens and reticle may be selectively positioned and aligned with the critical angle prism prior to installing the entire aligned subassembly within a refractometer housing.

The invention also encompasses a method whereby the optically critical components of a refractometer system are aligned prior to installing the components as a subassembly inside a refractometer housing. The method includes locating a critical angle prism on a subassembly frame; securing a compensating wedge mount to one end of a temperature responsive member, connecting the opposite end of the member to the frame, and temporarily supporting a compensating wedge in the mount. The procedure also requires supporting an objective lens and a reticle in the subassembly frame and cementing the various optical elements in position. The elements can be aligned by selectively adjusting the compensating wedge and reticle relative to the critical angle prism prior to, or subsequent to, being fixed in place.

FIGS. 4 and 5 are a top plan view and a front plan sectional view, respectively, showing a second embodiment of the present invention.

DESCRIPTION OF THE PREFERRED EMBODIMENTS

Figure 1:
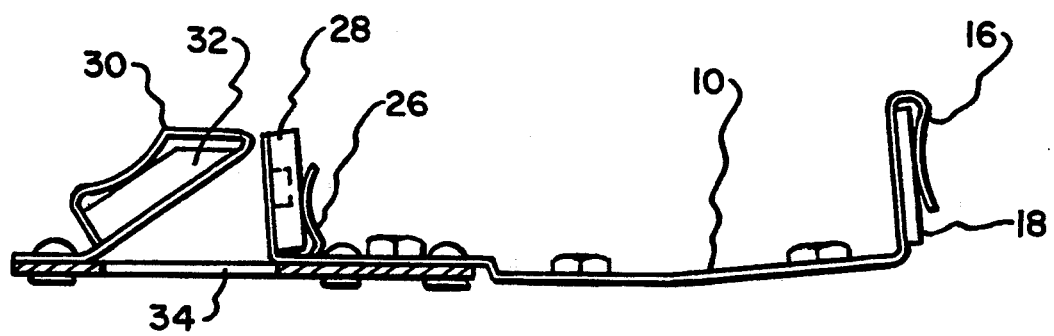
FIG. 1 is a schematic view illustrating a prior art subassembly with optical elements excluding a critical angle prism.
Figure 2:
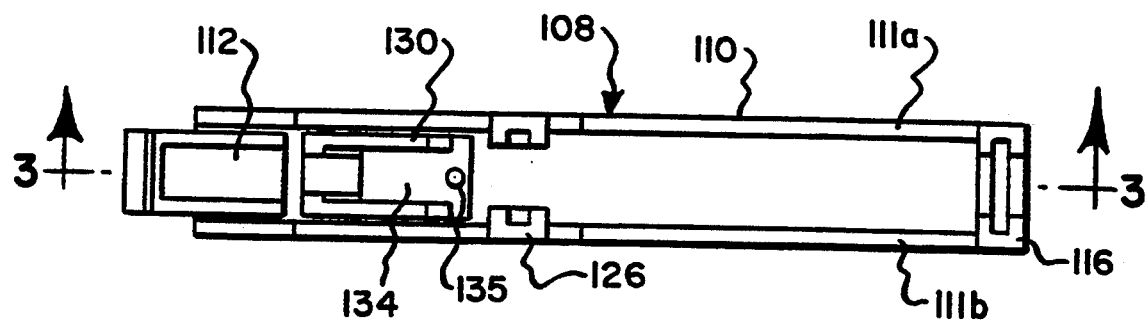
FIGS. 2 and 3 are a top plan view and a front plan sectional view, respectively, showing one embodiment of the present invention.
Figure 3:
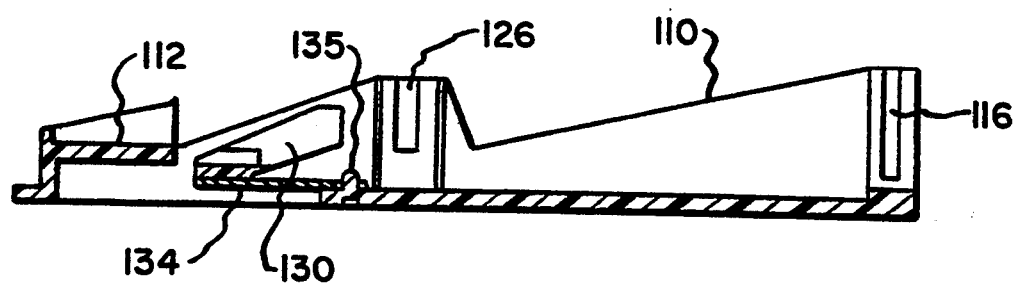

Turning now to FIGS. 2 and 3, one embodiment of the invention is shown. Subassembly frame 108 includes a one-piece elongated body 110 having opposing sides 111a and 111b, reference surface 112, reticle mount 116 and lens mount 126. Compensating wedge mount 130 is attached to one end of elongated temperature responsive member 134, with the other end of member 134 being fastened to body 110 by fastener 135. Reference surface 112 defines the location at which a critical angle prism is fixed to body 110, preferably by cementing it to surface 112. Reticle mount 116 and lens mount 126 are designed to slidably support a reticle and an objective lens, respectively, by friction. Wedge mount 130 is provided to frictionally support a compensating wedge. This embodiment permits the optical elements to be moved into alignment and then fixed in place to create a permanently aligned subassembly.

FIGS. 4 and 5 illustrate a second embodiment of the invention. Subassembly frame 208 includes a one-piece elongated body 210 having opposing sides 211a and 211b, and reference surface 212 for locating and supporting critical angle prism 214. Body 210 also has a reticle mount 216 for holding reticle 218. Reticle mount 216 is connected to body 210 by elastic reticle mount support member 220 which extends from bridge 221. Reticle adjustment screw 222 extends upwardly through retainer plate 224 and communicates with elastic member 220 at a point proximate to reticle mount 216. Lens mount 226 is formed as a part of body 210 to hold objective lens 228. Compensating wedge mount 230 holds compensating wedge 232. Wedge mount 230 is fastened to one end of elongated temperature responsive member 234 by rivet 236. Temperature responsive member 234 serves as an elongated lever which pivots about fulcrum 238 such that its opposite end, which has a slot 240, is engaged with biasing spring 242. Biasing spring 242 is preferably formed as an integral part of body 210 and extends from bridge 221. Biasing spring 242 has a protrusion 244 which is received within slot 240. Wedge adjustment and retaining screw 246 extends upwardly through body 210 into threaded engagement with temperature responsive member 234. By locating screw 246 between fulcrum 238 and biasing spring 242, temperature responsive member 234 is forced into engagement with fulcrum 238.

The second embodiment, like the first, permits alignment of all optically critical elements of the refractometer prior to their installation as a subassembly within a refractometer housing. To make an aligned subassembly, critical angle prism 214 is placed on reference surface 212. Compensating wedge mount 230 is riveted to temperature responsive member 234; member 234 is then set across fulcrum 238 and connected to body 210 using wedge adjustment and retaining screw 246. Compensating wedge 232 is placed in wedge mount 230, objective lens 228 is inserted in lens mount 226, and reticle 218 is inserted in reticle mount 216. Critical angle prism 214 is then fixed to body 210, as are objective lens 228 and reticle 218, preferably by cement. Compensating wedge 232 is fixed to wedge mount 230. Pursuant to known conventions in the art of refractometry, final alignment is conducted by alternately turning reticle adjustment screw 222 and wedge adjustment and retaining screw 246 to calibrate the instrument for at least two different refractive values.

Frame 208 is preferably molded as a unit from suitably rigid plastic. Glass reinforced polycarbonate will provide locational integrity and durability to preserve alignment of the optical elements fixed to it. Black plastic is preferred because it does not reflect incident light rays.

A completed subassembly eliminates the need for further optical alignment or adjustment of elements and is ready to be installed, preferably by cementing frame 208 to an inner surface of housing 248. An eyepiece 250 is connected to the end of housing 248 opposite critical angle prism 214, however the eyepiece 250 is used merely to magnify scale markings on reticle 218 and is not an optically critical component which needs to be aligned with the other optical elements. After focusing eyepiece 250, the entire unit may be hermetically sealed by conventional procedures.

While the present invention has been described with reference to two preferred embodiments which show a refractometer wherein the compensating wedge is moved by a temperature responsive member, one of ordinary skill in the art of temperature compensated, hand-held refractometers will understand that the claimed invention is not confined to such an arrangement. The spirit and scope of the invention encompass alternative refractometers, discussed above, wherein the objective lens or reticle is moved by a temperature responsive member, and those wherein all of the optical elements remain stationary.

What is claimed is:

1. A temperature compensated, hand-held refractometer comprising:
   a hollow housing;
   an elongated, one-piece subassembly frame insertable within said housing, said frame including a reference surface at a first end thereof for locating and supporting a critical angle prism, reticle mounting means at an opposite end thereof for slidably supporting a reticle, and lens mounting means between said ends for slidably supporting an objective lens;
   an elongated temperature responsive member engaging said frame and wedge mounting means connected to said member for slidably supporting a compensating wedge for movement with said member;
   a critical angle prism fixed to said reference surface, a reticle fixed to said reticle mounting means, an objective lens fixed to said lens mounting means, and a compensating wedge fixed to said wedge mounting means;
   reticle adjustment means for selectively moving said reticle to an aligned position while said frame is outside of said housing and wedge adjustment means for selectively moving said compensating wedge to an aligned position while said frame is outside of said housing; and
   an eyepiece attachable to said housing;
   whereby said reticle and compensating wedge may be aligned with said objective lens and said critical angle prism prior to installation of said frame within said housing.

2. A refractometer according to claim 1, wherein said reticle mounting means, wedge mounting means, and lens mounting means slidably support said reticle, compensating wedge, and objective lens, respectively, by friction.

3. A refractometer according to claim 1, wherein said reticle adjustment means includes an elongated elastic member integrally formed with and extending from said frame, said reticle mounting means being integral with and located at the distal end of said elastic member.

4. A refractometer according to claim 3, wherein said reticle adjustment means further includes at least one screw cooperating with said elastic member to selectively position said reticle mounting means.

5. A refractometer according to claim 1, wherein said wedge adjustment means includes a fulcrum integrally formed with said frame, said fulcrum being located between said reticle mounting means and said reference surface, said temperature responsive member being pivotal about said fulcrum, and at least one screw in threaded engagement with said member for pivoting said member about said fulcrum.

6. A refractometer according to claim 5, wherein said wedge adjustment means further includes biasing means integrally formed with said frame for urging said member in a first pivotal direction about said fulcrum.

7. A refractometer according to claim 6, wherein said biasing means includes a protrusion and said member includes a slot adapted to cooperate with said protrusion for laterally positioning said member.

8. A temperature compensated, hand-held refractometer subassembly frame comprising an elongated, one-piece, molded body, said body having two opposed sides stretching substantially the length of said body, a bridge laterally spanning said body from one of said opposed sides to the other of said opposed sides near a first end of said body, a critical angle prism reference surface at an opposite end of said body, said reference surface being substantially parallel to the longitudinal axis of said body, an elongated reticle mount support extending from said bridge in a direction away from said reference surface and substantially parallel to said sides, a reticle mount located at the distal end of said reticle mount support and extending in a direction substantially perpendicular to the longitudinal axis of said body, a temperature responsive member fulcrum located between said reference surface and said bridge, and an objective lens mount located between said reference surface and said reticle mount and extending in a direction substantially perpendicular to the longitudinal axis of said body.

9. A subassembly frame according to claim 8, wherein said body further comprises a temperature responsive member biasing spring extending from said bridge in a direction toward said fulcrum and substantially parallel to said sides.

10. A subassembly frame according to claim 9, wherein said biasing spring includes a temperature responsive member locating protrusion integral with and located at the distal end of said biasing spring.

11. A method of aligning optically critical components of a refractometer comprising the steps of:
 a) locating a critical angle prism at a reference position on a subassembly frame and fixing said prism to said frame at said reference position;
 b) attaching a compensating wedge mount to a temperature responsive member;
 c) adjustably attaching said temperature responsive member to said frame to permit selective alignment positioning of said wedge mount;
 d) slidably supporting a compensating wedge in said wedge mount;
 e) slidably supporting an objective lens in an objective lens mount integrally formed with said frame;
 f) slidably supporting a reticle in a reticle mount integrally formed with said frame, said reticle mount being adjustable to permit selective alignment positioning of said reticle;
 g) fixing said compensating wedge, objective lens, and reticle in their respective mounts; and
 h) selectively positioning said wedge mount and said reticle mount until said compensating wedge and reticle are aligned with said critical angle prism and said objective lens.

* * * * *